(12) United States Patent
Wong et al.

(10) Patent No.: US 10,525,163 B2
(45) Date of Patent: Jan. 7, 2020

(54) COLLAGEN BIOMATERIALS

(71) Applicant: Josephine Wong, Kuala Lampur (MY)

(72) Inventors: Josephine Wong, London (GB);
Robert Brown, London (GB)

(73) Assignee: Josephine Wong, Kuala Lumpur (MY)

( * ) Notice: Subject to any disclaimer, the term of this patent is extended or adjusted under 35 U.S.C. 154(b) by 0 days.

(21) Appl. No.: 15/316,403

(22) PCT Filed: Jun. 5, 2015

(86) PCT No.: PCT/GB2015/051651
§ 371 (c)(1),
(2) Date: Feb. 21, 2017

(87) PCT Pub. No.: WO2015/185942
PCT Pub. Date: Dec. 10, 2015

(65) Prior Publication Data
US 2017/0182212 A1      Jun. 29, 2017

(30) Foreign Application Priority Data

Jun. 6, 2014   (GB) .................................. 1410119.0

(51) Int. Cl.
| | | |
|---|---|---|
| *A61L 27/24* | (2006.01) | |
| *A61L 27/52* | (2006.01) | |
| *A61L 27/18* | (2006.01) | |
| *A61L 27/20* | (2006.01) | |
| *A61L 27/26* | (2006.01) | |
| *A61L 27/36* | (2006.01) | |
| *A61L 27/38* | (2006.01) | |

(52) U.S. Cl.
CPC ............. *A61L 27/24* (2013.01); *A61L 27/18* (2013.01); *A61L 27/20* (2013.01); *A61L 27/26* (2013.01); *A61L 27/3687* (2013.01); *A61L 27/3804* (2013.01); *A61L 27/52* (2013.01)

(58) Field of Classification Search
None
See application file for complete search history.

(56) References Cited

U.S. PATENT DOCUMENTS

| | | | | |
|---|---|---|---|---|
| 5,331,092 A | * | 7/1994 | Huc | ...................... A61L 15/325 435/174 |
| 6,790,454 B1 | * | 9/2004 | Abdul Malak | ..... A61L 27/3804 424/422 |
| 8,785,389 B2 | * | 7/2014 | Brown | .................... A61L 27/24 424/70.14 |
| 2013/0099407 A1 | | 4/2013 | Tully et al. | |

OTHER PUBLICATIONS

Su, W. F., Polymer size and polymer solutions, in Principles of polymer design and synthesis (2013) ISBN 978-3-642-38730-2, chapter 2, p. 14.*
Lee, Hwankyu et al, "A couarse-grained model for polyehtylene oxide and polyethylene glycol: conformation and hydrodynamics." J. Phys. Chem. B (2009) 113(40) p. 13186-13194.*
Brown, Robert A. et al, "Ultrarapid engineering of biomimetic materials and tissues: fabrication of nano- and microstructures by plastic compression." Adv. Funct. Mater. (2005) 15 p. 1762-1770.*
Grace, Lim Hui Yi and Wah, Tong Yen, "Effect of collagen gel structure on fibroblast phenotype." J. Emerg. Invest. (2012, p. 1-9.*
Steven, F. S. et al, "Polymeric collagenisolated from the human intestinal submucosa." Gut (1969) 10 p. 484-487.*
Steven, F. S. and Jackson, D. S., "Purification and amino acid composition of monomeric and polymeric collagen." Biochem. J. 1967) 104 p. 534-539.*
Wong et al., "Pre-crosslinked polymeric collagen in 3-D models of mechanically stiff tissues: Blended collagen polymer hydrogels for rapid layer fabrication", Acta Biomaterialia, Dec. 1, 2014, pp. 5005-5011, vol. 10, No. 12, Elsevier, Amsterdam, Netherlands.

* cited by examiner

*Primary Examiner* — Fred H Reynolds
(74) *Attorney, Agent, or Firm* — Pamela J. Sherwood; Bozicevic, Field & Francis LLP

(57) ABSTRACT

This invention relates to methods of producing collagen biomaterials by admixing (i) a solution of monomeric collagen, (ii) a solution of polymeric collagen, (ii) cargo particles, and (iv) a non-collagen blocking polymer, to produce a collagen solution. The collagen solution is then allowed to solidify to produce a collagen hydrogel. This may be useful in improving the stiffness of collagen hydrogel constructs and increasing the entrapment and retention of cargo particles.

10 Claims, 5 Drawing Sheets

COLLAGEN BIOMATERIALS

CROSS REFERENCE

This application claims benefit and is a 371 application of PCT Application No. PCT/GB2015/051651, filed Jun. 5, 2015, which claims benefit of G.B. Application No. 1410119.0, filed Jun. 6, 2014, which applications are incorporated herein by reference in their entirety.

FIELD

This invention relates to the production of collagen biomaterials.

BACKGROUND

Collagen is the major structural protein of human and animal connective tissues. It is widely accepted as a safe and natural biomaterial for the manufacture of a broad range of collagen-based food, cosmetic and medical products.

Collagen is commonly used in the construction of engineered bio-mimetic collagenous tissues for therapeutic applications. These bio-mimetic tissues are generally made from collagen gels produced from soluble monomeric collagen.

Collagen hydrogels formed from monomeric collagen may be readily seeded with cells. Collagen hydrogels with interstitially seeded (tissue relevant) cells have long been used in tissue engineering as cell compatible, simple, 3D models of living tissues. However, the gels rely on the fibrillogenesis (gelling) of collagen monomer around the cells and are themselves weak and relatively poorly organised.

Collagen hydrogels by definition contain vast amounts of water (>99%), resulting in limited matrix mechanical properties; much lower than the potential collective strength of the individual collagen fibrils. These matrix properties are known to affect cell behaviour (migration, proliferation and differentiation) and matrix mechanical properties are often improved by processes such as plastic compression (Brown, R et al. *Adv. Funct. Mater.* 15, 1762-1770 (2005); Hadjipanayi et al, J Tissue Eng Regen Med. (2011) July; 5(7): 505-19; WO2006/003442; WO2007/060459) and collagen crosslinking when modelling stiff tissues (such as skin and tendons).

Artificial cross-linking of collagen fibrils to improve the stiffness of the collagen matrix is cytotoxic. This prevents the seeding of interstitial cells at the outset and a lengthy and variable cell seeding stage is required to produce cellular cross-linked collagen biomaterials and constructs.

SUMMARY

The present inventors have recognized that matrix stiffness can be improved in collagen hydrogel constructs by blending polymeric and monomeric forms of collagen and the incorporation of non-collagenous blocking polymers into these stiff collagen hydrogel constructs can increase the entrapment and retention of cargo particles during compression and reduce the damage caused to interstitial cells.

An aspect of the invention provides a method of producing a collagen biomaterial,
admixing the following to produce a collagen solution (i) a solution of monomeric collagen, (ii) a solution of polymeric collagen, (ii) cargo particles, and (iv) a non-collagen blocking polymer, and
allowing the collagen solution to solidify to produce a collagen hydrogel.

In some preferred embodiments, the method may further comprise;
reducing the amount of liquid in the collagen hydrogel to produce a compressed collagen biomaterial.

Cargo particles may include mammalian cells, solid elements and particles, macromolecules, such as proteins, and therapeutic agents.

Other aspects of the invention provide collagen biomaterials produced by the methods of the invention and uses and applications thereof.

DETAILED DESCRIPTION

Figure 1:
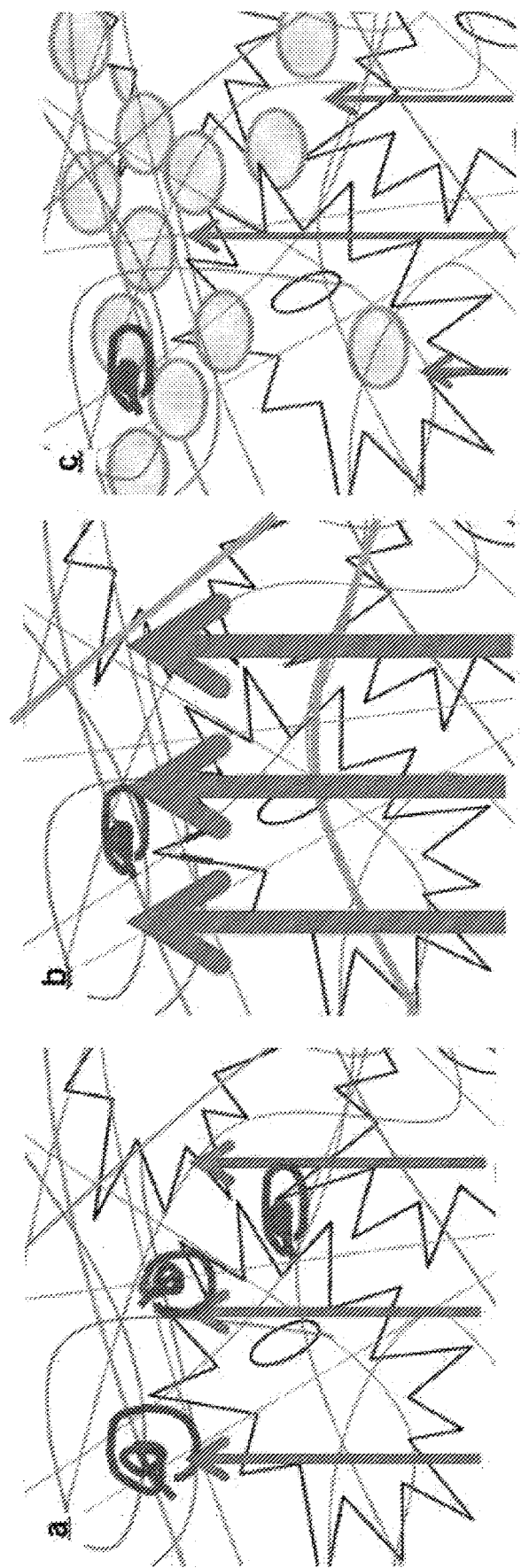
FIG. 1 shows a schematic representation of fluid flow, during plastic compression, within cellular a) conventional hydrogel b) blend (polymeric collagen containing) hydrogel and c) blend hydrogel containing large polymers/molecules. Fluid flow and (intrinsically present) non-associated collagen species are denoted by arrows and purple lines respectively. High fluid flow is damaging to cells.

The experiments herein show that stiff collagen hydrogels can be produced by blending polymeric and monomeric collagen. The compression of stiff collagen hydrogels containing blends of polymeric and monomeric collagen reduces the entrapment of mobile cargo particles, such as mammalian cells, solid elements and nanoparticles within the hydrogel. Compression may also damage mammalian cells entrapped in the hydrogel as cargo particles. However, cargo particle entrapment may be increased and cell damage reduced during compression by the incorporation of non-collagen blocking polymers into the collagen hydrogels.

The non-collagen blocking polymer incorporated into the collagen hydrogel acts as a blocking agent which reduces the rate of liquid flow out of the hydrogel. This improves nanoparticle/small molecule retention in the biomaterial during the liquid reduction and/or reduces that damage caused to the mammalian cells in the hydrogel from compression.

The non-collagen blocking polymer is preferably not bound to other components of the hydrogel and is mobile within the hydrogel. The non-collagen blocking polymer is a large, soluble polymer that is heterologous to the collagen scaffold of the hydrogel.

Suitable non-collagen blocking polymers have a hydrodynamic radius (Stokes radius) of at least 11 nm. For example, a non-collagen blocking polymer may have a hydrodynamic radius of 11 to 500 nm, 11 to 250 nm or 11 to 100 nm.

In some embodiments, the collagen blocking polymer may have a hydrodynamic radius (Stokes radius) of at least 11 nm and less than 100 nm, less than 50 nm or less than 30 nm.

Hydrodynamic radius may be measured by any convenient method including gel-permeation and gel-filtration chromatography (Dutta et al (2001) *Journal of Biological Physics* 27: 59-71; Uversky, V. N. (1993). *Biochemistry* 32 (48): 13288-98; Armstrong et al Biophys J. December 2004; 87(6): 4259-4270). Preferably, hydrodynamic radius is determined as set out in Armstrong et al (2004) supra.

Suitable non-collagen blocking polymers include natural polymers, such as dextran, xanthan gum, guar and starch, and synthetic polymers, such as polyethylene glycol, e.g. PEG400 or PEG1000, polyvinyl alcohol, poly(ethylene oxide), polyvinylpyrrolidone (PVP), hydroxyethylcellulose and carboxymethylcellulose.

The non-collagen blocking polymer may be present within the hydrogel at 1 to 100 mg/ml or 2 to 50 mg/ml, for example, 5 to 20 mg/ml, preferably about 10 mg/ml.

Collagen tissue contains two types of collagen. Monomeric collagen, which is acid soluble and forms short chains, represents up to 20% of the total collagen in collagen tissues. Monomeric collagen forms weak gels with random fibril organisation. Polymeric collagen represents 80% or more of the total collagen in collagen tissues.

A collagen solution for use in producing the biomaterials and constructs described herein comprises a blend or mixture of both polymeric and monomeric collagen. The collagen solution solidifies to produce a collagen hydrogel that comprises polymeric and monomeric collagen fibrils and an interstitial liquid.

The collagen in the collagen solution may be 20% to 100% (w/w), 30% to 80% (w/w), 35% to 70% (w/w), 40% to 60% (w/w) or 45% to 55% (w/w), preferably about 50% polymeric collagen. Following fibrillogenesis, 20% to 100% (w/w), 30% to 80% (w/w), 35% to 70% (w/w), 40% to 60% (w/w) or 45% to 55% (w/w), preferably about 50% of the collagen fibrils in the collagen hydrogel may be polymeric collagen fibrils.

Polymeric and monomeric collagen fibrils in the collagen hydrogel may be of any native fibril-forming collagen type, including collagen types I, II, III, V, VI, VII, IX and XI (II, IX, XI in cartilage tissues only) and combinations of these (e.g. I, III V or II, IX, XI etc). More preferably, the collagen fibrils are of collagen type I, II or III. For example, the fibrils may be collagen type I fibrils or combinations of types I, III and V or types II, IX and XI.

Polymeric collagen (PC) forms the major fraction of most collagen tissue. It is insoluble and comprises aligned strands of collagen fibres which are covalently cross-linked and organised into large diameter fibrils with few small oligomeric aggregates. The large diameter fibrils contain covalent intra-fibrillar cross-linkages.

Polymeric collagen may be purified from native collagen tissue by swelling the polymer at low pH into a clear solution/suspension, and then re-condensing/re-aggregating the collagen fibres by neutralisation (Steven F. S. (1967) Biochim. Biphys. Acta 140, 522-528; Schofield, J. D. et al (1971) Biochem. J. 124, 467-473; Steven, F. S. et al (1969) Gut 10, 484-487). For example, a polymeric collagen solution may be produced by a method comprising;

(i) depleting calcium from a sample of collagen tissue, for example by treatment with ethylenediaminetetraacetic acid (e.g. 0.5M EDTA)
(ii) dispersing the calcium depleted tissue sample in an acid solution, such as 0.5M acetic acid, to produce a tissue suspension,
(iii) neutralising the tissue suspension, for example with NaOH, to cause the polymeric collagen in the suspension to aggregate,
(iv) removing aggregated polymeric collagen from the neutralised tissue suspension,
(v) dispersing the aggregated polymeric collagen in an acidic solution to produce a polymeric collagen suspension,
(vi) neutralising the polymeric collagen suspension to cause the polymeric collagen in the suspension to aggregate,
(vii) removing aggregated polymeric collagen from the neutralised suspension,
(viii) optionally performing one or more repetitions of steps (v) to (vii), and
(ix) dispersing the aggregated polymeric collagen in an acidic solution to produce a purified polymeric collagen suspension Monomeric collagen (MC) forms up to 20% of total collagen in most collagen tissue. It is acid-soluble and forms short chains that are not cross-linked.

Monomeric collagen may be obtained from commercial suppliers or purified from native collagen tissue, such as rat skin or tail tendon, by swelling the polymer at low pH into a clear solution/suspension, and then condensing and removing cross-linked polymeric collagen, for example by salt fractionation.

A monomeric collagen solution for use in preparing a collagen hydrogel may be produced for example by neutralising a 90% acid-soluble collagen solution (e.g. 2.05 mg/ml in acetic acid) containing 10% cell culture medium e.g. using NaOH.

The collagen hydrogel is interstitially seeded with cargo particles.

Cargo particles are heterologous components that are sufficiently small to be mobile within the hydrogel. Cargo particles are artificially introduced into the collagen solution and are not found in polymeric or monomeric collagen preparations purified from collagen tissues using conventional techniques (see for example Steven, F. S. and Jackson, D. S. (1967), Biochem. J. 104, 534).

In some embodiments, the cargo particles are cells and the compressed collagen construct is cellular.

Cargo particles may include viable mammalian cells.

Mammalian cells interstitially seeded in the collagen hydrogel are not damaged by the liquid removal process and remain viable in the compressed collagen biomaterial (i.e. the compressed collagen biomaterial is cellular).

Mammalian cells may include muscle cells to provide contractile structures, vascular and/or neural cells to provide conductive elements, metabolically active secretory cells, such as liver cells, hormone synthesising cells, sebaceous cells, pancreatic islet cells or adrenal cortex cells to provide secretory structures, fibroblasts, such as dermal fibroblasts, skin keratinocytes, melanocytes (and combination layers of the two), Schwann cells for nerve implants, smooth muscle cells and endothelial cells for vessel structures, urothelial and smooth muscle cells for bladder/urethra structures, osteocytes, chondrocytes, and tendon cells for bone and tendon structures and stem cells, such as corneal (limbal) stem cells, skin epidermal stem cells, gut (intestinal) stem cells, orogenital stem cells, bronchial and other epithelial stem cells, bone marrow stem cells, growth plate stem cells.

In some preferred embodiments, the cells may be dermal fibroblasts, keratinocytes, melanocytes, stem cells or chondrocytes.

Cells may be distributed interstitially within the collagen hydrogel or the compressed collagen biomaterial in any arrangement. For example, the cells may be distributed homogeneously throughout the biomaterial or distributed in defined zones, regions or layers within the biomaterial.

Mammalian cells may be incorporated into the collagen solution under suitable conditions of temperature, neutral pH, ionic strength and sheer to maintain viability. Preferably, the collagen solution is neutralised before the cells are added. The cells may be added to the collagen solution, for example by pipette seeding followed by gentle mixing. In some embodiments, the cells are added to the collagen solution after the polymeric collagen, monomeric collagen and non-collagen blocking polymer.

The initial cell density in the collagen solution may be from about $1 \times 10^4$ to $1 \times 10^7$ cells per ml, more preferably from about $1 \times 10^5$ to $1 \times 10^6$ cells per ml.

Liquid removal compresses the hydrogel and reduces its volume. Cell density may increase 2 fold or more, 10 fold or more, 100 fold or more or 200 fold or more in the compressed collagen biomaterial, in accordance with the reduction in volume.

In other embodiments, the cargo particles are not cells and the compressed collagen construct is acellular.

Cargo particles may include solid elements.

Solid elements may include tubes, such as carbon nanotubes; particles such as metal or hard tissue particles, nanoparticles, magnetic particles and imaging particles, such as radio-opaque, ultrasound reflective or fluorescent particles; fibres, such as capillary filaments; and vesicles such as lipid/phosphor lipid vesicles, liposomes and slow-release drug vesicles.

Hard tissue particles may be approximately 100-500 microns in diameter and may be of any solid material or mineral, for example porous ceramic, tricalcium phosphate, silicone, glass, bioglass, phosphate glass, hydroxapatite, or bone mineral preparations (from native bone removal of organic phase).

Hard tissue particles may be incorporated into the compressed collagen biomaterial along with osteoblasts or chondrocytes, to produce an artificial bone or calcified cartilage substitute tissue. The ratio of particles to biomaterial and cells will depend on the particle size and the tissue properties required (e.g. dense or loose packed hard tissue).

Cargo particles may include therapeutic agents. Compressed collagen biomaterials incorporating therapeutic agents may be useful as capsules, depots or implants which release the therapeutic agent in situ in a patient or may themselves incorporate capsules, liposomes, vesicles or depots containing therapeutic agents.

Therapeutic agents may include small organic molecules, proteins, such as antibody molecules, hormones, cytokines, chemokines, growth factors, viruses, nucleic acid molecules, such as aptamers or antisense or sense suppression molecules, vectors, antibiotics, or micro-organisms. The therapeutic agents may be loaded into nanoparticles or other bodies or free in the interstitial liquid.

The collagen hydrogel as described herein is formed by the coalescence and elongation (fibrillogenesis) of collagen fibrils, as the fibrils form a continuous network around the aqueous interstitial liquid which originally held the collagen solutions. For example, triple helical collagen monomers may be initially dissolved in dilute acid and then induced to polymerise to fibrils (e.g. at 37° and neutral pH). As fibrillogenesis occurs, there is a phase change and the solid network of fibrils 'supports' the remaining interstitial liquid in approximately the same volume and shape—i.e. it gels.

Phase transition from soluble monomer to solid polymer through fibrillogenesis is characteristic of a collagen hydrogel. Gels are distinct from 'sponges', which may be formed from pre-polymerised fibres.

A collagen hydrogel may comprise >90% (w/w), >95% (w/w) or >99% (w/w) interstitial liquid. The interstitial liquid is an aqueous liquid. For example, the liquid may be water with solutes such as salts and proteins dissolved therein. In some embodiments, the interstitial liquid is a cell culture medium suitable for the growth and proliferation of cells.

Liquid removal and compression of the collagen hydrogel increases its stiffness relative to untreated collagen hydrogel.

The liquid content of the collagen hydrogel is reduced to compress the hydrogel and produce the compressed collagen biomaterial. The amount of interstitial liquid in the compressed collagen biomaterial is therefore less than in the collagen hydrogel.

Compression of the hydrogel reduces its volume, such that the hydrogel retains or substantially retains its new volume, even after the liquid content is reduced. This compression reduces the distance between collagen fibrils and increases the number of contact points between adjacent fibrils in the biomaterial, increasing the stiffness of the compressed collagen biomaterial. Liquid removal is a rapid, cell-independent process which results from subjecting the hydrogel to a physical treatment, such as an external force or capillary action, which draws or expels interstitial liquid from the hydrogel.

Suitable methods for removing interstitial liquid from the collagen hydrogel are well-known in the art and are described, for example in Brown, R et al. *Adv. Funct. Mater.* 15, 1762-1770 (2005); Hadjipanayi et al, J Tissue Eng Regen Med. (2011) July; 5(7):505-19; WO2006/003442 and WO2007/060459. For example, the interstitial liquid may be expelled or drawn out of the gel.

In some preferred embodiments, the amount of liquid in the collagen hydrogel may be reduced by contacting the gel with an absorbent body such that liquid moves from the hydrogel into the body by capillary action.

The absorbent body may, for example, be paper, in particular blotting paper. The absorbent body may be removed from the gel after sufficient liquid has been drawn from the hydrogel to effect the desired compression.

Liquid may be removed with one or more defined vectors or directions and the interstitial liquid may move from the gel through a defined surface of the hydrogel into the absorbent body. The surface of the gel through which liquid passes when the hydrogel is compressed is called the fluid leaving surface (FLS).

The collagen hydrogel may be confined or partially confined during liquid removal. A permeable support may be used to confine the FLS of the collagen hydrogel, while other surfaces are confined by impermeable supports. Liquids may be expelled through hydrogel surfaces which are supported or confined by a permeable support. Hydrogel surfaces confined by permeable supports during liquid removal will be fluid leaving surfaces. The non-FLS surfaces of the hydrogel may be confined by impermeable supports which prevent egress of interstitial liquid, such that liquid removal is directed through the fluid leaving surfaces only.

The non-collagen blocking polymer within the hydrogel reduces the initial rate of flow of the liquid from the hydrogel. For example, liquid may move from the hydrogel at a rate of <0.65 ml/min.

The non-collagen blocking polymer in hydrogel reduces the rate of flow of the liquid from the hydrogel. For example, liquid may move from the hydrogel at an average rate of <0.13 ml/min over 5 mins.

The collagen hydrogel may be contacted with the absorbent body until no further liquid is drawn from the hydrogel into the body (i.e. compression is complete).

The non-collagen blocking polymer increases the time required for complete compression of the hydrogel. For example, the collagen hydrogel is contacted with the absorbent body for 30 mins or more.

The amount or extent of liquid reduction may be varied, depending on the application of the biomaterial. For example, the amount of liquid in the collagen hydrogel may be reduced by at least 50%, at least 60%, at least 70%, at least 80%, at least 90%, at least 99% or at least 99.9% of the original liquid content of the hydrogel.

For example, the volume of the hydrogel may be reduced by 50% or more, 60% or more, 70% or more, 80% or more, 90% or more, 95% or more, 99% or more, or 99.9% or more by removal of interstitial liquid.

Preferably, some interstitial liquid remains after compaction, for example at least 10%, at least 1% or at least 0.1% of the original liquid content of the hydrogel. This allows the survival of mammalian cells within the compressed collagen construct.

In preferred embodiments, the hydrogel or compressed collagen construct is not subjected to drying or desiccation, for example heat, freeze-, airflow or vacuum drying, before, during or after liquid removal, as dehydration kills cells and damages biomaterial structure.

The presence of the non-collagen blocking polymer in the hydrogel prevents damage to mammalian cells during liquid removal and compression. At least 70%, at least 80%, at least 90% or at least 95% of the mammalian cells in the collagen hydrogel may remain viable in the compressed collagen biomaterial.

The presence of the non-collagen blocking polymer in the hydrogel improves the entrapment of cargo particles during liquid removal and compression. At least 50%, at least 60%, at least 70%, at least 80%, at least 90%, or at least 95% of the cargo particles in the collagen hydrogel may be present in the compressed collagen biomaterial.

After solidification, the compressed collagen biomaterial may be stored, used for tissue engineering applications or processed further.

To reduce and/or prevent cell death or damage, a compressed collagen biomaterial comprising mammalian cells may be stored under conditions which maintain viability but which do not support cell growth, until ready for use. For example, the biomaterial may be stored at low temperature e.g. 0 to 10° C. or frozen (<0° C.) in the presence of a cryoprotectant. The biomaterial can be stored in cell culture medium at 37° C. for short periods of time. In some embodiments, the biomaterial is not subjected to drying or desiccation, for example heat, airflow or vacuum drying, as dehydration kills cells and damages biomaterial structure.

Another aspect of the invention provides a compressed collagen biomaterial comprising polymeric collagen fibrils, monomeric collagen fibrils, cargo particles and a non-collagen blocking polymer.

The compressed collagen biomaterial may be produced by compressing a collagen hydrogel as described herein and may have reduced liquid content and increased stiffness relative to the uncompressed collagen hydrogel.

Suitable polymeric and monomeric collagen solutions, cargo particles and non-collagen blocking polymers are described in more detail above.

Another aspect of the invention provides a kit comprising;
a polymeric collagen solution,
a monomeric collagen solution,
cargo particles selected from mammalian cells, solid elements and therapeutic agents; and
a non-collagen blocking polymer.

Suitable polymeric and monomeric collagen solutions, cargo particles and non-collagen blocking polymers are described in more detail above.

The kit may include instructions for use in a method of production of a compressed collagen biomaterial as described above.

A kit may include one or more other reagents required for the method, such as buffer solutions, cell culture media and absorbent bodies.

A kit may include one or more articles for performance of the method, such as vessels, multiwell plates, and reagent handling containers (such components generally being sterile).

Compressed collagen biomaterials described herein may be useful as 3-dimensional model tissues for toxicological, pharmacological and pathogen screening as well as other research purposes. The compressed collagen biomaterials may also be useful as coatings, fillers and for conventional (e.g. metal or plastic) prosthetic implants or as capsules, depots or implants for controlled in situ drug release, as well as applications in therapy, pharmaceutical development, cell culture, orthopaedics, dermatology and wound healing.

Compressed collagen biomaterials may also be useful in the production of tissue equivalent implants.

A tissue equivalent implant is a material for implantation into an individual to repair or replace endogenous tissue, which, for example, may be damaged or diseased. Examples of tissues which may be repaired or replaced by tissue equivalent implants include nerves, tendons, ligaments, cartilage, skin, fascia, bone, urogenital elements, liver, cardiopulmonary tissues, kidney, ocular tissues, such as the cornea, blood vessels, intestine, and glands.

Diseased or damaged tissue may for example result from arthritides, neuro-muscle injury/degeneration, musculo-tendenous failure and age-degeneration, poor regeneration after trauma (e.g. burns), tissue necrosis or surgical resection (e.g. tumour surgery).

To produce a tissue equivalent implant, the compressed collagen biomaterials may undergo additional processing, e.g. tissue culture, moulding and/or shaping.

After production, the compressed collagen biomaterial may be subjected to tissue culture to allow resident cells in the biomaterial to deposit minor components and remodel the collagen material.

The compressed collagen biomaterial may be shaped, cut or moulded into any convenient implant form, for example, a patch, block, tube, tape, strip, ring, sphere, toroid, capillary, roll, sheet or thread to produce a tissue equivalent implant. The final shape of the implant will depend on the particular context in which it is to be used. In some embodiments, the implant may have a pliable form which is suitable for further shaping.

In some embodiments, a sheet or strip of compressed collagen biomaterial may be rolled up or folded to form a multi-layered construct e.g. a roll. This multi-layered construct may be used directly as a tissue equivalent implant or may be further cut, shaped or moulded as required. In some embodiments, the multi-layered construct may be plastically compacted to adhere multiple layers together, achieve the desired dimensions, increase cell density or to improve other properties.

Other aspects of the invention relate to compressed collagen biomaterial as described herein for use as a tissue equivalent implant and the use of a compressed collagen biomaterial as described herein in the manufacture of a medicament for use as a tissue equivalent implant, for example for the replacement, repair or supplementation of damaged or dysfunctional tissue.

A tissue equivalent implant may be suitable for a therapeutic application described above.

Another aspect of the invention provides a tissue equivalent implant comprising or consisting of a compressed collagen biomaterial produced or producible by a method described herein.

Another aspect of the invention provides a method of treatment of a damaged or defective tissue in an individual comprising;

fixing a tissue equivalent implant as described herein to said tissue to repair, supplement and/or replace said tissue.

The implant may be fixed by any convenient technique. For example, it may be sutured or glued in place.

Implants produced from the compressed collagen biomaterials described herein will take sutures and can be sutured surgically into body sites even when under muscle load.

Other aspects of the invention relate to hydrogels and compressed biomaterials made from polymeric collagens. A method of producing a biomaterial may comprise;

admixing the following to produce a collagen solution (i) a solution of polymeric collagen (ii) cargo particles, and (iii) a heterologous blocking polymer, allowing the collagen solution to solidify to produce a hydrogel.

In some preferred embodiments, the method may further comprise;

reducing the amount of liquid in the hydrogel to produce a compressed polymeric collagen biomaterial comprising the cargo particles, and the mobile blocking polymer.

Solution of polymeric collagen may be produced as described in WO2011/007152.

The above description of the aspects of the invention relating to blended polymeric and monomeric collagen solutions and hydrogels applies mutatis mutandis to aspects relating to polymeric collagen gel solutions and hydrogels.

Other aspects of the invention relate to hydrogels and compressed biomaterials made from non-collagen scaffold polymers (i.e. non-collagen biomaterials). A method of producing a biomaterial may comprise;

admixing the following to produce a gel solution (i) a solution of a non-collagen scaffold polymer (ii) cargo particles, and (iii) a heterologous blocking polymer, allowing the gel solution to solidify to produce a hydrogel.

In some preferred embodiments, the method may further comprise;

reducing the amount of liquid in the hydrogel to produce a compressed biomaterial comprising the cargo particles, and the mobile blocking polymer.

Suitable non-collagen scaffold polymers aggregate to form hydrogels comprising fibres of the scaffold polymer and interstitial liquid. Suitable polymers include naturally occurring polymers, for example proteins, such as silk, fibrin, fibronectin, or elastin, glycoproteins or polysaccharides such as chitin, or cellulose; or synthetic polymers, for example organic polymers such as polylactone, polyglycone and polycapryolactone and inorganic polymers such as phosphate glass.

The blocking polymer is heterologous to the non-collagen scaffold polymer and is mobile within the hydrogel. Suitable blocking polymers are described above.

The above description of the aspects of the invention relating to collagen solutions and hydrogels applies mutatis mutandis to aspects relating to non-collagen gel solutions and hydrogels.

Various further aspects and embodiments of the present invention will be apparent to those skilled in the art in view of the present disclosure.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the figures described above and the following tables.

Table 1 shows the average compression rate (±standard deviation (SD)) at first 30 seconds (initial rate) and 5 minutes of compression, for collagen treated with pepsin for increasing time or increasing concentration of large polymers. Time to complete compression was noted as the time where compression rates reached zero (correct to 2d.p.).

Experiments
1. Materials and Methods
Collagen Hydrogels

Acellular hydrogels were prepared, on ice, by neutralising a 90% rat tail acid-soluble type-I collagen (2.05 mg/ml in acetic acid, First link, UK) containing 10% 10× Minimum Essential Medium (MEM) (Gibco life technologies, UK) using 5M and 1M sodium hydroxide (NaOH). For cellular hydrogels, 10% of the acid-soluble solution was substituted with cell containing 10% Dulbecco's modified eagle medium (DMEM supplemented with 10% foetal calf serum and 1% penicillin streptomycin, Sigma-Aldrich; containing cells), only added after neutralisation.

Where specified, blended stiff collagen hydrogels were produce by substituting half the volume of acid-soluble collagen with a solution of polymeric collagen (adjusted to ~2 mg/ml in 0.5M acetic acid). Briefly, polymeric (pre-crosslinked) collagen was extracted from homogenised calf tendons though 0.5M ethylenediaminetetraacetic acid (EDTA; Sigma-Aldrich) treatment (Steven, F. *Biochim. Biophys. Acta.* 140, 522-528, 1967) for 24 hours, with at least one change of solution. The treated tendons were washed twice in distilled water before placing in 0.5M acetic acid (causing collagen fibrils in the tendon mass to expand). Polymeric collagen was collected by shear aggregation during neutralisation (using NaOH). The recovered collagen was repeatedly (at least twice) expanded and recovered from 0.5M acetic acid to remove impurities trapped between collagen fibrils. Equal volume of chloroform (BDH laboratory supplies) was used for sterilisation.

Pepsin Treatment

Pepsin treatment converted tropocollagen (conventional gelling collagen) into atelocollagen as a source of mobile collagen species. The latter associates less readily with adjacent collagen molecules during fibrillogenesis, and remains mobile within the hydrogel (at the time of compression), potentially blocking the FLS. Pepsin (Sigma-Aldrich) was dissolved in 0.5M acetic acid (2.5 mg/ml) and added 1:99 to acid soluble type-I collagen at 4° C. (on stirrer). At 0, 1.5, 3, 6, 9, 24, 48, 72, 94 hours after pepsin addition, the collagen solution was neutralised (as detailed above). 2.5 ml of the solution was incubated in 24-well plates at 37° C., 5% $CO_2$ for 30 minutes. The compression rate of resultant gels was measured (see below).

Large Polymer

Large polymers, which remain mobile during fibrillogenesis, were incorporated into collagen hydrogels to increase blockage at the FLS.

Large polymers such as fibrinogen (340 kDa; Sigma-Aldrich) in 0.9% saline, dextran (500 kDa; Fisher Bioreagents) or poly(ethylene oxide) (PEG; 400 kDa or 1000 kDa, Sigma-Aldrich) in deionised water, were made to a concentration of 0, 2, 5, 10 or 20 mg/ml. Ficoll™ 400 (Sigma-Aldrich) was made to 10 or 50 mg/ml in deionised water. Polymer solutions (10%) were mixed into 90% neutralised collagen solution (on ice), prior to transferring 2.5 ml into 24-well plates for incubation (30 minutes; 37° C., 5% $CO_2$) and subsequent measurement of compression rate.

Measuring Rate of Hydrogel Compression

Hydrogels were plastically compressed using a paper roll plunger (Whatman grade 1 chromatography paper, 95×4 cm), separated from the hydrogel by two well-sized paper discs (Whatman, grade 1 paper) designed to protect the hydrogel. The rate of compression was measured as a function of mass gained by the plungers with time (measured every 30 seconds in the first 5 minutes of compression, then every minute subsequently), until no further mass gain was detected.

Cellular Blended Collagen Gels 10 mg/ml PEG 400 kDa resulted in optimal control of compression rates, and was used in blended (polymeric) collagen gels containing human dermal fibroblasts (1.5 ml gel; 15,000 cells/gel). The blend gel was produced and compressed as described above. Cell activity within the gel was measured by Alamar blue assays. For the assay, 10% Alamar blue (AbD, Serotec) was added to 90% phenol-red free DMEM (Sigma-Aldrich), of which 0.5 ml was added to each sample and incubated for 4 hours (37° C., 5% $CO_2$). 100 µl of the Alamar blue solution was transferred into a 96-well microplate spectrophotometer (in duplicates; MR700 microplate reader, Dynatech Laboratories) for absorbance reading at 510 and 590 nm.

Nano Particle Entrapment

Hyaluronan nanoparticles (HA-NP) conjugated with fitc (500 nm) was used to study the efficiency of nanoparticle entrapment within compressed hydrogels in the presence of FLS blocking polymers. 1 mg/ml HA-NP was dissolved in deionised water and vortexed for 30 seconds prior to use.

10% 1 mg/ml HA-NP was added to the neutralised collagen solution containing 70% acid-soluble type-I collagen, 10% 10×MEM and 10% PEG (400 kDa), prior to gelation in 24-well plates (30 minutes, 37° C. (dry incubator)). Resultant hydrogels were fully compressed (uncompressed gels as controls) and dissolved in 1 ml 0.2% collagenase I solution (in water, Gibco, UK) at 37° ° (on a shaker) for up to 40 minutes. The resultant HA-NP containing solution was diluted 1:2252, in deionised water, prior to absorbance reading (LS 50B, Luminescence Spectrometer, Perkin Elmer; 490 nm excitation, 525 nm emission wavelengths).

Statistics

Statistical significance was determined by one-way ANOVA (LSD post-hoc) for data on compression rates. For all other experiments, an independent sample t-test was used. Confidence intervals were set at $p<0.05$.

2. Results

The rates of initial (first 30 seconds) and at 5 minutes of compression, with pepsin treatment of collagen or large polymer incorporation, are summarised in table 1. Pepsin treatment of acid-soluble collagen did not result in decreased rates of compression. The time to complete compression remained consistently lower than control hydrogels (without pepsin treatment), suggesting any mobile species generated by the treatment did not result in the blockage of interfibrillar 'pores' at the FLS. Therefore these mobile species must either be smaller than these pores, or that the decrease in tropocollagen (gel forming collagen) resulted in enlarged 'pores' within the hydrogel, rendering it less effective in catching mobile species.

Figure 2:
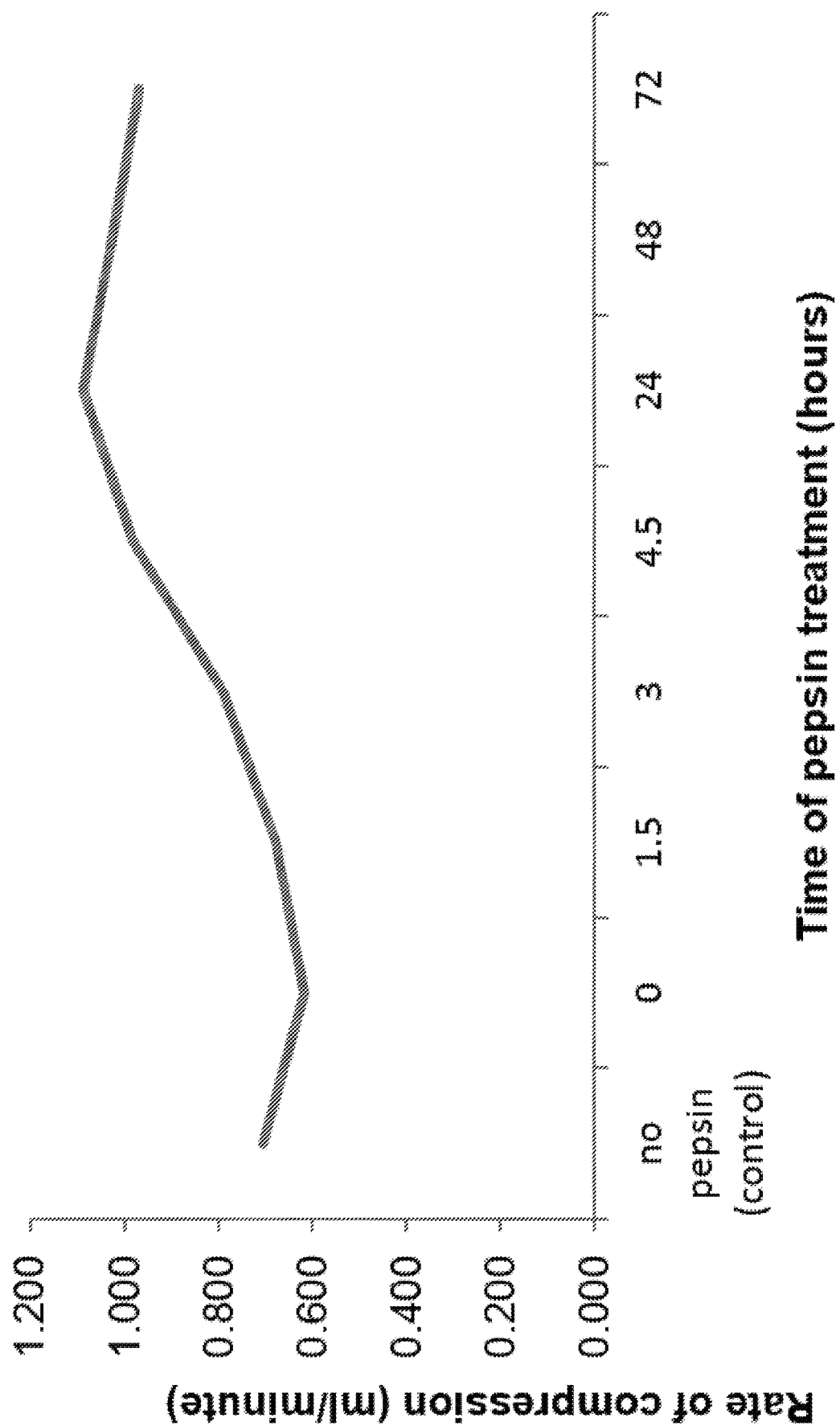
FIG. 2 shows the initial (first 30 seconds) compression rate of hydrogels with increasing pepsin treatment time (prior to neutralization).

The rate of collagen compression continued to increase up to 24 hours of pepsin treatment. With further treatment time, compression rates showed signs of decreasing from the fastest initial rate (1.089±0.152 ml/minute), at 24 hours of pepsin treatment (FIG. 2).

Figure 3:
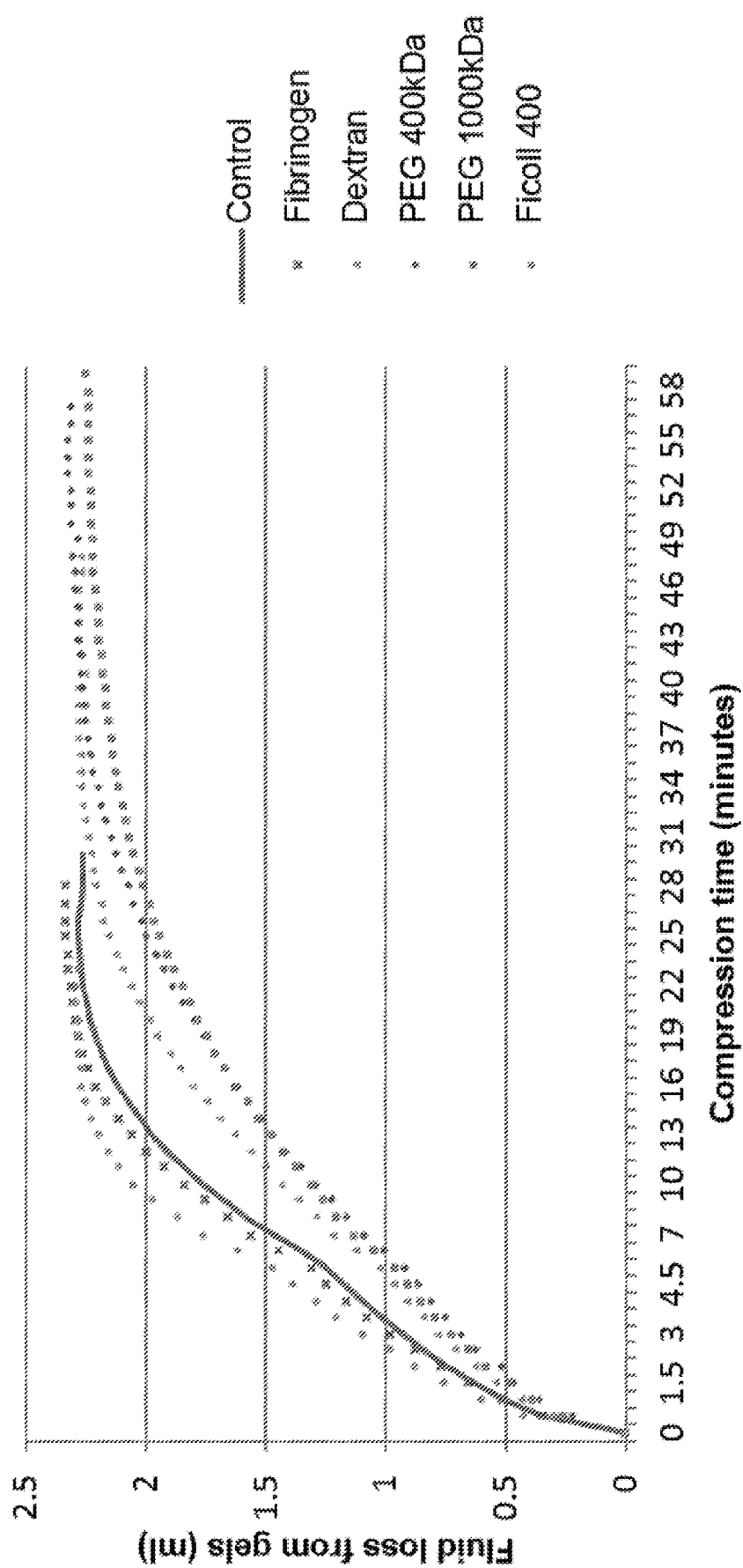
FIG. 3 shows the compression profiles of 2.5 ml hydrogels containing 10% 10 mg/ml polymers (no polymer control). Fluid loss from hydrogels during compression was measured as mass (fluid) gain by absorbent plungers over time.

Large polymer incorporation was more effective in decreasing compression rate, with the optimal concentration of polymers being 10 mg/ml PEG (400 and 1000 kDa) ($p\leq0.001$ and $p=0.001$ respectively) (FIG. 3). 10 mg/ml fibrinogen ($p=0.837$) or dextran ($p=0.085$) did not slow compression rates, however, interestingly, a lower concentration of fibrinogen (5 mg/ml) was able to decrease compression rates relative to control gels ($p=0.006$). However, when Ficoll™ 400 (10 mg/ml) was added to collagen hydrogels, the rate of compression increased significantly ($p=0.002$) contrary to expectation.

Figure 4:
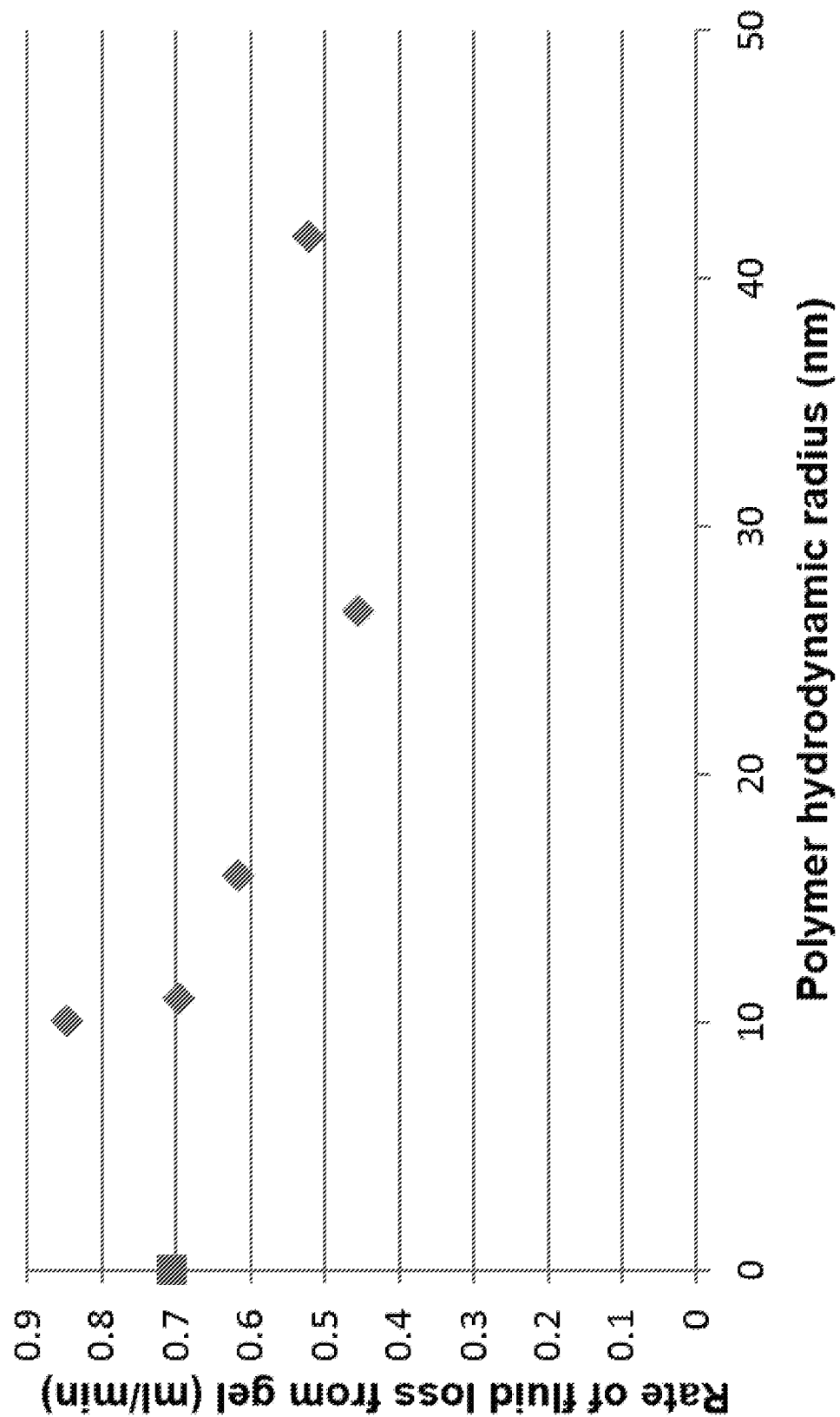
FIG. 4 shows the correlation between polymer hydrodynamic radii and their respective initial (first 30 seconds) compression rate. All polymer concentration was consistent at 10 mg/ml.

The decrease in compression rate correlated with the Stoke's radius of polymers, independent to its molecular weight. In general, the larger the hydrodynamic radius, the more effective the polymer was as a blocking agent at the FLS. The hydrodynamic radius for the fibrinogen, dextran, PEG 400 kDa, PEG 1000 kDa and Ficoll 400 were 10.95, 15.9, 26.56, 41.63 and ~10 nm respectively (adapted from Armstrong, J. et al. *Biophys J.* 87, 4259-4270, 2004) (FIG. 4). Fibrinogen and ficoll400, with stoke radius <11 nm, did not have a slowing effect on the rate of compression. Conversely, polymers larger than PEG 400 kDa (26.56 nm; i.e. PEG1000 kDa) did not further slow the initial compression rate ($p=0.147$). The effect of larger polymers can be seen further downstream of the compression time, as hydrogels with the larger polymer can only be completely compressed over a longer period of time.

Figure 5:
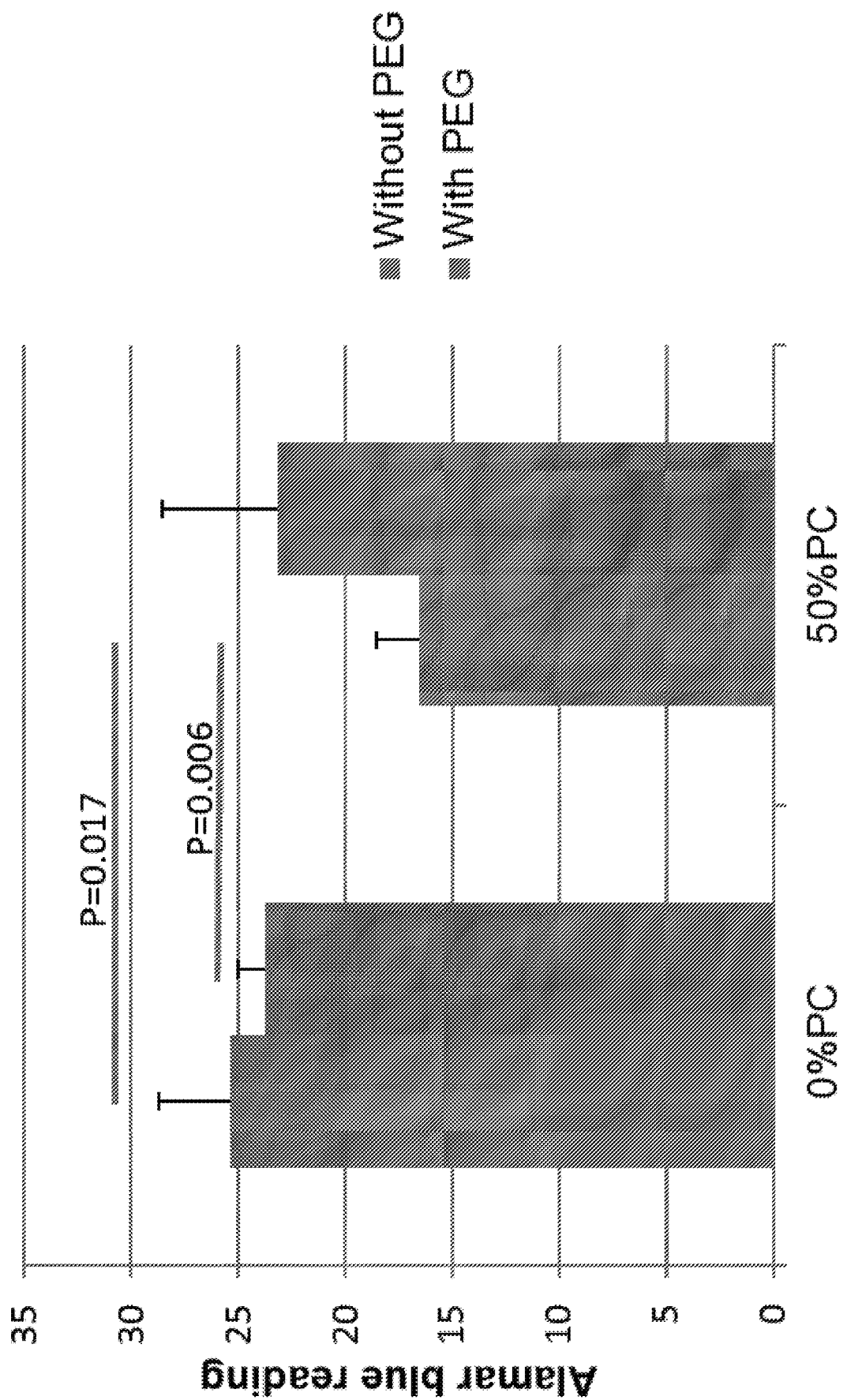
FIG. 5 shows the total cell activity in polymeric collagen blend gels 1 day after compression. Cell activity within blend gels, with or without 10% PEG incorporation, was compared to (control) conventional monomeric collagen hydrogels.

10 mg/ml PEG (400 kDa) resulted in optimal decrease in initial compression rates, and so was used in blend gels with interstitially seeded cells. Alamar blue readings of (conventional) control gels were similar at 25.35±3.33 and 23.77±1.20, with or without PEG. In blended gels, cells were damaged in the absence of PEG (reading of 16.53±1.98), which was significantly lowered from control gels (p=0.017). However, interstitial cells were rescued from damage in the presence of PEG, where cell activity detected was similar to controls (FIG. 5).

Controlled compression rates through blockage of the FLS are applicable in fast-compressing hydrogels, where shear stress may cause damage to resident cells. Alternatively, the filtration effect may also be used for improving nanoparticle/small molecule retention within a hydrogel during plastic compression.

Rates of collagen compression were controllable using artificially introduced mobile species incorporated into hydrogels. Mobile species contained in hydrogels contribute to the blockage of the FLS during compression, forming a physical barrier to fluid movement. The extent of FLS blockage, hence control of compression rate was found to be dependent on the hydrodynamic radius of molecules (polymers), rather than its molecular size. In this study, polymers with stokes radii <11 nm did not affect the initial compression rate of the collagen hydrogel, with optimal polymer size at ~26.6 nm. Further increase in polymer hydrodynamic size did not further decrease the initial compression rate of the hydrogel. The larger polymer size did, however, affect the continuous compression rates. The reason for focusing on the initial compression rate (so rate at the first 30 seconds of compression) is because this is highest rate throughout the compression process, and likely to be most detrimental to cells/NP loss.

The limitation on blocking agent size may explain the inability of pepsin treated collagen, as mobile collagen species, in controlling hydrogel compression rates. Although, the loss of the binding regions in the telopeptides renders the collagen less able to associate with adjacent collagen molecules, and so remain free-floating within the hydrogel at the time of compression, these atelocollagen molecules are likely smaller than the critical size of 11 nm, therefore cannot block the FLS effectively. As a result, compression rates did not decrease as hypothesised, but actually increased with pepsin treatment time as the mobile atelocollagen species were produced at the cost of gel-forming tropocollagen species—meaning less fibrils were involved in gel formation; therefore larger 'pores'.

Compression of blended gels caused significant cell death, but this was reversed by incorporating mobile polymer molecules, such as PEG. This both slowed the fluid flow and spared resident cells. Molecules with less than ~11 nm Strokes radius did not result in slowed compression rates. However, PEG (400 kDa and 1000 kDa), with the highest (of those tested) hydrodynamic radius was effective in decreasing the rate of initial compression. This enabled the rapid production of stiff tissue models (3 fold increase in modulus) with cells seeded interstitially. Additionally, the ability to finely control the extent of plastic compression, hence matrix stiffness, has potential implications for control of cell behavior.

TABLE 1

| Treatment/polymer | n | Compression rate at 30 seconds (average rate (ml/minute) ± SD) | Fluid loss rates at 5 minutes compression (average rate (ml/minute) ± SD) | Time to complete compression (minutes) |
|---|---|---|---|---|
| Control 0% saline | 14 | 0.706 ± 0.090 | 0.141 ± 0.045 | 25 |
| Control 10% saline | 9 | 0.691 ± 0.083 | 0.135 ± 0.024 | 26 |
| Pepsin 0 hours | 6 | 0.616 ± 0.148 | 0.148 ± 0.024 | 25 |
| Pepsin 1.5 hours | 6 | 0.743 ± 0.077 | 0.160 ± 0.025 | 20 |
| Pepsin 3 hours | 6 | 0.791 ± 0.081 | 0.168 ± 0.010 | 17 |
| Pepsin 4.5 hours | 3 | 0.983 ± 0.248 | 0.115 ± 0.092 | 14 |
| Pepsin 24 hours | 9 | 1.089 ± 0.152 | 0.184 ± 0.046 | 13 |
| Pepsin 48 hours | 9 | 1.027 ± 0.160 | 0.230 ± 0.152 | 20 |
| Pepsin 72 hours | 6 | 0.970 ± 0.173 | 0.146 ± 0.043 | 19 |
| Fibrinogen 2 mg/ml | 15 | 0.660 ± 0.114 | 0.139 ± 0.026 | 28 |
| Fibrinogen 5 mg/ml | 15 | 0.582 ± 0.119 | 0.141 ± 0.026 | 27 |
| Fibrinogen 10 mg/ml | 9 | 0.698 ± 0.097 | 0.138 ± 0.034 | 26 |
| Fibrinogen 20 mg/ml | 6 | 0.915 ± 0.107 | 0.177 ± 0.025 | 17 |
| Dextran 2 mg/ml | 14 | 0.650 ± 0.085 | 0.124 ± 0.015 | 31 |
| Dextran 5 mg/ml | 15 | 0.615 ± 0.090 | 0.131 ± 0.022 | 32 |
| Dextran 10 mg/ml | 12 | 0.618 ± 0.075 | 0.115 ± 0.013 | 36 |
| Dextran 20 mg/ml | 9 | 0.631 ± 0.053 | 0.125 ± 0.027 | 36 |
| PEG 400 kDa 2 mg/ml | 9 | 0.691 ± 0.085 | 0.144 ± 0.014 | 26 |
| PEG 400 kDa 5 mg/ml | 9 | 0.566 ± 0.080 | 0.123 ± 0.017 | 35 |
| PEG 400 kDa 10 mg/ml | 9 | 0.456 ± 0.121 | 0.107 ± 0.018 | 43 |
| PEG 400 kDa 20 mg/ml | 6 | 0.636 ± 0.054 | 0.097 ± 0.005 | 50 |
| PEG 1000 kDa 10 mg/ml | 6 | 0.524 ± 0.028 | 0.103 ± 0.017 | 50 |
| PEG 1000 kDa 20 mg/ml | 6 | 0.564 ± 0.051 | 0.095 ± 0.019 | 71 |
| Ficoll 400 ™ 10 mg/ml | 6 | 0.846 ± 0.084 | 0.165 ± 0.038 | 20 |
| Ficoll 400 ™ 50 mg/ml | 6 | 0.908 ± 0.089 | 0.172 ± 0.024 | 16 |

The invention claimed is:
1. A method of producing a collagen biomaterial, admixing the following to produce a collagen solution (i) a solution of monomeric collagen produced by neutralising a solution of monomeric collagen dissolved in acid, (ii) a solution of polymeric collagen, (ii) viable mammalian cells and (iv) a non-collagen blocking polymer, wherein 40% to 60% (w/w) of the collagen in the collagen solution is polymeric collagen,
allowing the collagen solution to solidify to produce a collagen hydrogel, and
reducing the amount of liquid in the collagen hydrogel by contacting the gel with an absorbent body to produce a compressed collagen biomaterial comprising viable mammalian cells.

2. A method according to claim 1 wherein the blocking polymer is dextran or polyethylene glycol.

3. A method according to claim 1 wherein the collagen solution comprises 2 mg/ml to 50 mg/ml blocking polymer.

4. A method according to claim 1 wherein the polymeric collagen solution is produced by
(i) depleting calcium from a sample of collagen tissue,
(ii) dispersing the calcium depleted tissue sample in an acid solution to produce a tissue suspension,
(iii) neutralising the tissue suspension to cause the polymeric collagen in the suspension to aggregate,
(iv) removing aggregated polymeric collagen from the neutralised tissue suspension,
(v) dispersing the aggregated polymeric collagen in an acidic solution to produce a polymeric collagen suspension,
(vi) neutralising the polymeric collagen suspension to cause the polymeric collagen in the suspension to aggregate,
(vii) removing aggregated polymeric collagen from the neutralised suspension,
(viii) optionally performing one or more repetitions of steps (v) to (vii), and
(ix) dispersing the aggregated polymeric collagen in an acidic solution.

5. A method according to claim 4 wherein the acid soluble collagen solution comprises cell culture medium.

6. A method according to claim 1 wherein the compressed collagen biomaterial has reduced liquid content and increased stiffness relative to the collagen hydrogel.

7. A method according to claim 1 wherein the amount of liquid in the hydrogel is reduced at a rate of <0.65 ml/min.

8. A method according to claim 1 wherein the amount of liquid in the hydrogel is reduced at an average rate of <0.13 ml/min over 5 mins.

9. A method according to claim 1 wherein the amount of liquid in the hydrogel is reduced by at least 50%.

10. A method according to claim 1 wherein the collagen biomaterial comprises at least $1 \times 10^4$ viable mammalian cells per ml.

* * * * *